United States Patent [19]

Gilchrist et al.

[11] Patent Number: 4,906,616
[45] Date of Patent: Mar. 6, 1990

[54] HYDROLYZED SODIUM CASEIN COMPOSITIONS FOR DIALYSIS PROCEDURES

[76] Inventors: Thomas Gilchrist, 67 Midton Road; William Manson, 14 Longbank Drive, both of AYR, Strathclyde, United Kingdom

[21] Appl. No.: 307,131

[22] Filed: Feb. 6, 1989

Related U.S. Application Data

[63] Continuation of Ser. No. 51,747, filed as PCT GB86/00507 on Aug. 27, 1986, published as WO87/01286 on Mar. 12, 1987, abandoned.

[30] Foreign Application Priority Data

Aug. 31, 1985 [GB]  United Kingdom ................ 8521712

[51] Int. Cl.$^4$ ............................................. A61K 37/18
[52] U.S. Cl. ........................................... 514/21; 514/2; 514/8; 514/12; 514/13; 514/14; 514/15; 514/16; 514/17; 514/18; 530/360; 530/361; 530/402; 530/407; 530/427; 530/832; 530/833; 435/268; 435/272
[58] Field of Search .............. 530/360, 361, 402, 407, 530/427, 832, 833; 435/268, 272; 514/2, 8, 21, 12, 13, 14, 15, 16, 17, 18

[56] References Cited

U.S. PATENT DOCUMENTS

| | | | |
|---|---|---|---|
| 4,179,338 | 12/1979 | Gordon | 435/173 |
| 4,309,417 | 1/1982 | Staples et al. | 514/21 |
| 4,339,433 | 7/1982 | Kartinos et al. | 514/2 |
| 4,361,587 | 11/1982 | Brule et al. | 435/69 |
| 4,427,658 | 1/1984 | Maubois et al. | 435/68 |
| 4,462,990 | 7/1984 | Jolles et al. | 435/69 |
| 4,495,176 | 1/1985 | Brule et al. | 530/407 |
| 4,604,379 | 8/1986 | Twardowski et al. | 514/21 |

FOREIGN PATENT DOCUMENTS 1039562  10/1978  Canada.
WO82/03987  11/1982  World Int. Prop. O..

OTHER PUBLICATIONS

Klein et al., Chem. Abs., 106, 23227a, Jan. 26, 1987 (Pub. date of original reference is 1986).
Meiji Seika Kaisha, Ltd., Chem. Abs. 45:148923k, 1981.
Nazar'ev et al., Chem. Abs., 97:159431r.
Oreopoulos et al., CA 93:165635u, 1980.

*Primary Examiner*—Margaret Moskowitz
*Assistant Examiner*—Jeff Kushan
*Attorney, Agent, or Firm*—Nixon & Vanderhye

[57]  ABSTRACT

A medicinal composition, particularly but not exclusively for use in fluids for medical dialysis, contains, as an agent for maintaining the osmolality of the fluid, a protein hydrolysate resulting from the action of a proteolytic enzyme on the sodium caseinate fraction of milk protein. The enzyme is preferably trypsin but other proteolytic enzymes and enzyme mixtures may be used, examples being chymotrypsin, pancreatin and pronase.

The method of production involves treating the sodium caseinate in aqueous medium with the enzyme at the appropriate pH and temperature for optimum enzyme activity. The product of the enzymic hydrolysis, after filtration through a bacterial filter, adjustment of the osmolality to an appropriate level of around 300 mOsm/Kg and the pH to physiological level of about 6.6 and addition of physiological salt levels, constitutes the final product.

8 Claims, No Drawings

HYDROLYZED SODIUM CASEIN COMPOSITIONS FOR DIALYSIS PROCEDURES

This application is a continuation of application Serial No. 051,747 filed as PCT GB86/00507 on Aug. 27, 1986, published as WO87/01286 on Mar. 12, 1987, now abandoned.

This invention relates to a composition having medicinal applications. More particularly, the invention relates to a fluid for use in medical dialysis procedures, particularly, but not exclusively, peritoneal dialysis.

In human body, solutes transfer from one body fluid to another by diffusion processes which include dialysis, osmosis and ultrafiltration (hereafter referred to simply as "dialysis"). Unwanted solutes, toxins and excess water are transferred from the bloodstream by dialysis in the kidneys for excretion from the body. In the event of kidney malfunction, the indicated medical treatment is kidney transplantation or, alternatively, extracorporeal haemodialysis. The preferred treatment is transplantation but, of course, this depends on the availability of donor kidneys of compatible tissue type. The surgical procedure is lengthy, and therefore expensive in manpower and equipment costs, and, although controllable to a great extent by drug administration, rejection of the transplanted kidney may occur. Transplantation, however, remains the preferred treatment as the patients may thereafter lead a more or less normal lifestyle.

Haemodialysis is a substitute for kidney transplantation. Depending on the severity of the renal malfunction, patients require more or less frequent sessions of dialysis. Blood is withdrawn from the patient's bloodstream and passed through a dialyser wherein the blood is brought into contact with a selectively permeably membrane, of cellulosic or synthetic polymeric material for example, the remote side of which contacts a dialysis fluid. By the laws of diffusion, solutes in the blood are transported across the membrane into the dialysis fluid and water is removed by ultrafiltration.

Haemodialysis is normally carried out under medical supervision in the out-patients department of hospitals although it can be done by the patient at home should he be capable of scrupulous observation of procedures after training. The absence of suitable conditions in the home or inabliity of the patient for one reason or another to observe the rules of procedure may preclude home dialysis. Dialysis machines are expensive and require a substantial amount of maintenance by way of routine sterilisation.

Haemodialysis is extremely restricting to the patient. For example, if leaving the vicinity of the treatment centre he has to make arrangements to be treated at a dialysis unit in the locale of his destination. In summary, then, renal dialysis is an extremely restricting form of treatment to the patient who has to attend hospital for dialysis and it requires a great deal of patient cooperation and attention to procedural details if it is to be carried out at home. The hardware associated with the procedure is also expensive.

Peritoneal dialysis is now a well-established procedure which may be used as a substitute for extracorporeal haemodialysis for those patients for whom, because of some medical condition other than the renal failure itself, the use of haemodialysis is contra-indicated or is simply not available.

In peritoneal dialysis, a dialysis fluid is introduced via a catheter into the peritoneal cavity in the abdomen of the patient and removal of toxins and water takes place across the peritoneum which acts as the semi-permeable membrane. The peritoneal cavity is flooded with the fluid, left for an appropriate lapse of time, and then drained.

In Continuous Ambulatory Peritoneal Dialysis (CAPD), a catheter is permanently implanted by surgery through the abdominal wall of the patient and it is through this catheter that the dialysis liquid is introduced, commonly, because procedures are simple, by the patient himself from a flexible sachet of the sterile fluid. Once the fluid has been introduced, the patient simple rolls up the sachet, stores it in a pocket in his clothing, and is then free to continue normal activity while dialysis takes place. Later, he drains the spend fluid under gravity back into the sachet for disposal and introduces a fresh batch. Thus, dialysis is continuous and this has the advantage over periodic sessions of dialysis that intermittent disruption of the body chemistry of the patient is avoided. The frequency of change of the fluid varies from patient to patient but may be about four times in each twenty-four hour period.

As indicated previously, saccaharides, glucose being the most common, are included in the dialysis fluids to impart the necessary osmotic gradient. Almost any substance which is introduced into the peritoneal cavity will find its way eventually into the bloodstream and this passage is increased by the presence of breaks in the integrity of the peritoneal membrane, a condition which is not uncommon in patients who require the treatment. While the body may be quite capable of metabolising the additional sugar, the long term effect is undesirable and in certain patients, such as diabetics, constitutes an unacceptable medical hazard, and may require the additional complication of the patient having to introduce insulin into the dialysis fluid.

It has been previously proposed to use as the osmotic agent, oligo- and poly-saccharides. However, should these materials penetrate through the peritoneal membrane hydrolysis may occur resulting in depolymerisation and the same unacceptable condition associated with simple sugars arises. Substances such as sorbitol, xylitol, polyglucoses and fructose have been investigated for application in peritoneal dialysis but have not found wide acceptance.

Amino acid mixtures are widely used in medicine for the treatment of diverse medical conditions and appear to have potential for use as osmotic agents in dialysis fluids. They are non-toxic and are well tolerated by the body but, being of low molecular weight and small size they tend to penetrate the peritoneal membrane very easily and so rapidly that loss of the osmotic gradient can occur resulting in reverse flow of solutes from the dialysis fluid into the circulation. However, previous work on this subject has established the non-toxicity of these substances.

An object of the present invention is to provide a medicinal composition for particular use in fluid for medical dialysis treatments.

According to the present invention there is provided a dialysis fluid comprising an aqueous solution containing as an osmotic agent a peptide-containing hydrolysate of milk protein.

Preferably, the protein is sodium caseinate.

Preferably also the hydrolysate is prepared by enzymic hydrolysis using a proteolytic enzyme such as trypsin, chymotrypsin, pancreatin, and pronase, of which trypsin is most preferred. However, numerous such enzymes are available and may be used as deemed necessary or desirable.

The osmolality of the solution is preferably in the range of from 100 to 400 mOsm/Kg, and most preferably in the region of 300 mOsm/Kg.

The expression "milk" as used herein is to be understood as encompassing the milk of any mammal. Although, in normal practice, bovine milk will be the preferred material, there may be instances where other mammalian milk may be preferred.

Normally the fluid will contain physiological concentrations of salts and other material, for example, one or more of sodium, calcium, magnesium, chloride, citrate and lactate and, optionally, magnesium, which are well-known additions to such fluids.

The present invention also provides a medicinal composition comprising a hydrolysate of sodium caseinate.

The medicinal comosition of this invention finds application not only as an osmotic agent in dialysis fluids but generally in proteinaceous medicinal preparations. For example, the protein hydrolysate of the invention may be included as a skin nutrient in dermatological or cosmetic preparations: it may also be used as a dietary supplement for the treatment of medical conditions which are caused by or produce nitrogen deficiency.

The mixture of peptides of this invention can be derived by enzymic action from sodium caseinate which is essentially a mixture of four proteins, namely alpha-S1, alphs-S2, beta and kappa-caseins. These occur in bovine milk and each is of known constant chemical composition and structure. Sodium caseinate is a commercial product, which is produced by fractionation of milk proteins and is advantageous in that it is available in high purity and of reliably known and predictable composition unlike some other fractions which tend to have variable and unpredictable composition. Treatment of sodium caseinate with a proteolytic enzyme of known specificity of action produces a peptide mixture of highly predictable and reproducible composition, which, according to the invention, may be varied by selection of the enzyme or mixture of enzymes employed. The composition of the peptide mixture can therefore be varied to ensure that it contains a substantial proportion of peptides having properties suitable for the production of a satisfactory osmotic gradient for use in standard dialysis procedures. This main requirement is satisfied by peptides have molecular weights in the region of 1000 (i.e. having 9 and 10 amino acid residues on average) and solubilities such that an aqueous solution of up to about 10 percent by weight can be achieved.

A typical example of the production of a peptide mixture for producing the osmotic gradient in dialysis, is afforded by the action of trypsin on sodium caseinate. The peptide mixture which results is composed of about 10 percent by weight of of peptides having from two to five amino acid residues, about 40 percent by weight having from six to eighteen residues and the remainder having in excess of eighteen residues. The theoretical average number of amino acid residues in the three categories mentioned are three, ten and thirty-two, corresponding to molecular weights of 330, 1100 and 3500 respectively. The proportion of those having chains of approximately ten amino acids may be increased at the expense of the longer chain length peptides by further treatment with one or more other proteolytic enzymes such as chymotrypsin or pancreatin.

After completion of the enzymic hydrolysis, the reaction mixture may be heat-sterilised and filtered to destroy and remove the enzymes present and thereby ensure that no proteolytic activity is transferred to the peritoneum during dialysis. However, it may be necessary or desirable to purify the peptide solution further by passage through a column of ion exchange resin. Sterilisation of the dialysis solution may be effected by micropore filtration which is a generally acceptable process for such solutions, or it may be radiation sterilised. It is not believed that autoclaving would be a suitable sterilisation procedure as the peptides may be degraded by the high temperatures encountered in such a process. It is possible, however, that autoclaving, if insisted upon might be done without any damage of significance.

The use of peptides to provide the osmotic gradient in dialysis has inherent advantages over the sugar-based solutions used hitherto. The molecular size of the bulk of the peptides (about molecular weight 1100 and greater) ensures that diffusion across the peritoneal membrane will be minimal. This has four important consequences. First, the osmolality of the peptide solution will be maintained for a much longer period than with glucose and amino acid solutions since both glucose and amino acids diffuse very rapidly across the membrane with concomitant reduction in the osmotic effectiveness of the solution in the peritoneum. for this reason the peptide solution will exert a greater osmotic effect over a longer period of time and hence require less frequent replacement of the dialysis fluid with a corresponding reduction in the risk of infection. Second, the absence of glucose removes a complicating factor in the treatment of diabetic patients and in the long term treatment of all patients. Third, any leakage of small peptides into the patient's bloodstream will present no metabolic problems and, indeed, may provide a small but useful supplement to the nitrogen content of the patient's diet. Fourth, the glucose-based solutions previously proposed have to be adjusted to pH for 5.3 to 5.5 or thereabouts to prevent degradation of the glucose during heatsterilisation: since the peptide-based solution of the present invention does not suffer from this disadvantage, it may be used at normal physiological pH value of around 6.6, which is, of course clinically desirable.

The present invention has been discussed herein in the context of peritoneal dialysis. However, similar considerations apply to other types of medical dialysis procedures such as haemodialysis and the invention is applicable to other dialysis procedures.

Protein hydrolysate derived from sodium caseinate as starting material have advantages accruing from that selection of starting material itself in that, beginning with sodium caseinate which, as previously mentioned, is of high purity and of more or less constant composition compared with other milk protein fractions, the peptide product also has this inherent purity and reproducible composition. On completion of the enzymic hydrolysis, the reaction requires only filtration and sterilisation to give the final product.

Hydrolysates of other milk protein fractions may be prepared in the manner described hereinbefore. For example, hydrolysates may be prepared from the whey fraction and also from beta-lactoglobulin and alpha-lactalbumin. The whey fraction suffers from the disadvantage that it has rather indefinite chemical composition and contains a number of residual proteins which are different to remove and this has the potention for non-reporducibility and contamination of the product hydrolysate. The beta-lactoglobulin and alpha-lactalbumin fractions are of known and constant composition and do allow reproducible hydrolysates to be prepared. However, there is no commercial advantage in using these starting materials rather than the casein fraction since they are more difficult to obtain on the market and are prohibitively expensive. There is no technical advantage in the hydrolysates of the lactoglobulin and lactalbumin hyrolysates which makes them any more preferable to the casein hydrolysates with which this invention is principally concerned. However, circumstances amy arise when these other hydolysates may have some hitherto unrecognised medical effect which would merit the additional expense involved in their preparation.

The protein hydrolysate of the invention is used as a dialysis fluid in the aqueous solution hereinbefore defined. However, the invention also includes solid protein hydrolysate obtained from the said aqueous solution by freeze drying or like process. The dried material may have advantage in shipping, as the additional weight of the water is avoided thus lowering shipping costs. For use in dialysis the dry material is simply reconstituted by dissolution in water. For use in other medicinal applications, the dried material may be formulated with the appropriate base composition.

The invention will now be described, by way of illustration, in the following Example.

EXAMPLE 1

To a volume 100 ml of a 6% by weight solution of commercially available sodium caseinate, M/5 sodium hydroxide was added dropwise to adjust the pH to 7.3. To th pH-adjusted solution, 20 mg of crystalline trypsin, dissolved in 5 ml of 0.001M hydrochloric acid, were added.

The mixture was maintained at a temperature of 20° C. and, with an automatic systems using glass electrodes, the pH was monitored and maintained at 7.3 by titration with M/5 sodium hydroxide to neutralise the acid liberated by the action of the trypsin on the caseinate. The hydrolysis reaction was complete in around 2 hours.

Thereafter, the pH was reduced to 6.6 by titration with M/5 hydrochloric acid.

To the solution thus obtained, there was added physiological amounts of sodium, calcium, chloride and lactate and, optionally, magnesium, as follows: Sodium ion: 135-145 m.equiv./liter; Calcium ion: 2.2-2.5 m.equiv./liter; Chloride ion: 90-100 m.equiv./liter; Lactate ion: 33-35 m.equiv./liter; (Magnesium ion: zero-2.0 m.equiv./liter).

The solution was then sterilised by filtration through a microporous bacterial filter of pore size 0.45 microns. The resulting solution was sterile and free of any residual enzyme activity. The osmolality of the solution was adjusted to 300 mOsm/Kg.

Preliminary pertitoneal dialyses were performed on non-uremic laboratory rats. This involved injection of 5 ml of the above solution into the peritoneal cavity. No ill-effects were observed. The solution was neither toxic nor immunogenic and was effective as a dialysis agent.

We claim:

1. In a dialysis process for removing water and biological toxins from body fluids by ultrafiltration wherein said body fluids contact a dialysis fluid through a semipermeable barrier, the improvement which comprises employing a peptide-containing proteolytic enzyme hydrolysate of sodium caseinate as an osmotic agent in the dialysis fluid, said hydrolysate being present in an amount effective to cause ultrafiltration.

2. A process according to claim 1 wherein the dialysis fluid additionally contains physiological salts, and a buffering agent, said salts and said agent being present in amounts effective to cause ultrafiltration of water and biological toxins into said fluid.

3. A process according to claim 1 wherein the proteolytic enzyme is trypsin, chymotrypsin, pancreatin, pronase or mixtures thereof.

4. A process according to claim 1 wherein the dialysis fluid has an osmolality of from about 100 to about 400 mOsm/Kg.

5. A process according to claim 4 wherein the osmolality is about 300 mOsm/Kg.

6. A process according to claim 1 wherein the dialysis fluid has a pH of about 6.6.

7. A process according to claim 2 wherein the physiological salts comprise ions selected from the group consisting of sodium, calcium, chloride, lactate, citrate and magnesium.

8. A process according to claim 7 wherein the concentration of the physiological salts is 135-145 meq/l sodium ions, 2.2-2.5 meq/l calcium ions, 90-100 meq/l chloride ions, 33-35 meq/l lactate ions, 0-2 meq/l magnesium ions, and mixtures thereof.

* * * * *